United States Patent [19]

Ringuet et al.

[11] Patent Number: 5,219,878

[45] Date of Patent: Jun. 15, 1993

[54] TETRAPYRROLE HYDROXYALKYLAMIDE PHOTOCHEMOTHERAPEUTIC AGENTS

[75] Inventors: Michel M. Ringuet, Trois Rivieres; James C. Kennedy; Roy H. Pottier, both of Kingston, all of Canada

[73] Assignee: Queen's University, Kingston, Canada

[21] Appl. No.: 807,341

[22] Filed: Dec. 16, 1991

Related U.S. Application Data

[63] Continuation-in-part of Ser. No. 593,867, Oct. 5, 1990, abandoned.

[51] Int. Cl.$^5$ .................. A01N 43/38; A61K 31/40
[52] U.S. Cl. .................. 514/410; 514/427; 540/145
[58] Field of Search .............. 514/410, 427; 540/145

[56] References Cited

U.S. PATENT DOCUMENTS

| | | | |
|---|---|---|---|
| 4,675,338 | 6/1987 | Bommer et al. | 514/410 |
| 4,837,221 | 6/1989 | Bonnett et al. | 514/410 |
| 4,851,403 | 7/1989 | Picker et al. | 514/185 |
| 4,920,143 | 4/1990 | Levy et al. | 514/410 |
| 4,932,934 | 7/1990 | Dougherty et al. | 514/410 |
| 4,968,715 | 11/1990 | Dougherty et al. | 514/410 |
| 4,992,257 | 2/1991 | Bonnett et al. | 514/410 |
| 4,996,233 | 2/1991 | Horrobin | 514/427 |
| 5,002,962 | 3/1991 | Pandey et al. | 514/410 |
| 5,079,262 | 1/1992 | Kennedy et al. | 514/561 |
| 5,087,636 | 2/1992 | Jamieson et al. | 514/410 |

Primary Examiner—Nathan M. Nutter
Attorney, Agent, or Firm—Richard J. Hicks

[57] ABSTRACT

This invention relates to new preparations which are valuable for photodetection and photochemotherapy of tumors and malignant tissues. The active compounds of these therapeutic preparations are mono-, di- or polyamides of an amino alcohol and a cyclic tetrapyrrole containing at least one carboxyl group. The general structure of these active compounds is $$(ZNHCO)_n X$$

wherein Z is the amino alcohol molecule less the amino group, X is the tetrapyrrole molecule less a carboxyl group, and "n" is an integer from 1 to 8.

10 Claims, No Drawings

TETRAPYRROLE HYDROXYALKYLAMIDE PHOTOCHEMOTHERAPEUTIC AGENTS

CROSS REFERENCE TO RELATED APPLICATION

This application is a continuation-in-part of U.S. application Ser. No. 593,867 filed 5 October 1990 and now abandoned.

FIELD OF THE INVENTION

This invention relates to a novel class of compounds which have photochemotherapeutic properties and are utilizable for photodetection and photochemotherapy of tumors and malignant tissues.

BACKGROUND OF THE INVENTION

Photodynamic therapy is an experimental form of treatment for cancer. It involves the localized or systemic administration of a photosensitizing compound or a metabolic precursor thereof, followed by exposure of the malignant tissue and adjacent normal tissues to photoactivating light. The tissue specificity of the resultant phototoxic damage is determined largely (though not entirely) by the relative concentrations of the photosensitizer in each tissue at the time of its exposure to the photoactivating light. Following systemic administration, certain derivatives of porphyrins, phthalocyanines, and chlorins accumulate preferentially within malignant tissues. At present a proprietary preparation of hematoporphyrin derivatives known under the tradename "Photofrin ® II" is undergoing clinical evaluation for the treatment of carcinomas involving the bladder, esophagus, lung, brain, and other anatomical sites. In addition, 5-aminolevulinic acid, a precursor of protoporphyrin IX in the biosynthetic pathway for heme, is now being used to selectively induce photosensitizing concentrations of protoporphyrin IX in basal cell carcinomas and squamous cell carcinomas as described in U.S. patent application Ser. No. 386,414 which is assigned to the present assignee. In suitable clinical circumstances, both "Photofrin ® II" and protoporphyrin IX induced by 5-aminolevulinic acid show a clinically useful degree of specificity for malignant tissues. However, not all porphyrins, phthalocyanines, or chlorins accumulate preferentially in tumors.

Injections of hematoporphyrin derivatives such as, but not limited to, Photofrin ® II cause a clinically significant degree of skin photosensitization that persists for at least two weeks and sometimes for as long as four months. During this photosensitive period the patient must avoid exposure to sunlight, even sunlight that has been filtered through window glass. Clearly this deleterious side effect causes considerable inconvenience to patients and severely limits the clinical usefulness of photodynamic therapy.

It is known that as malignant tumors enlarge from a single cell to a palpable nodule, their growth pattern is such that certain areas of tumor develop an inadequate blood supply. The cells in such zones are both poorly nourished and hypoxic. Some of these cells die, but others merely reduce their metabolic activity to a basal level. Such cells are relatively resistant to destruction by X-rays and gamma-rays, since (i) molecular oxygen is required for some of the radiation chemistry that can cause DNA damage and cell death, and (ii) quiescent cells are relatively resistant to radiation damage. Hypoxic and poorly nourished cells tend to be resistant to many types of chemotherapeutic agents also. Chemotherapeutic agents usually enter tissues via the blood, and malignant cells whose blood supply is inadequate may not receive a lethal dose. In addition the toxicity of many common chemotherapeutic agents is restricted primarily to cells that are in cell cycle. Consequently, malignant cells that are poorly nourished and/or hypoxic may survive courses of radiotherapy and/or chemotherapy that otherwise might have been curative. Such surviving cells may proliferate subsequently to cause a recurrence of the cancer.

Thus, a drug which shows sufficient preferential toxicity for hypoxic cells may be given in doses that should kill the hypoxic cells in tumors without causing unacceptable toxicity to the normally-oxygenated cells of non-malignant tissues. Such a drug might not be curative if given as the sole therapy, since only some of the cells in tumors are hypoxic but it would be a very useful adjunct to radiotherapy and/or chemotherapy, since these tend to kill well oxygenated cells preferentially. For example, certain nitro-containing compounds accumulate preferentially in hypoxic tissues where they cause preferential toxicity for the hypoxic cells.

Like most drugs, photochemotherapeutic agents usually enter malignant tissues by diffusion from capillaries. As a result, zones of tissue that are poorly supplied with capillaries will be exposed to relatively low concentrations of the compound, perhaps too low to be therapeutically effective, unless the compound has a special affinity for hypoxic or necrotic tissue. The primary mechanism by which most photosensitizers kill cells require effective contact between a molecule of photosensitizers and a molecule of oxygen. The probability that enough such contacts will take place within hypoxic tissue will be reduced if the concentration of the photosensitizer is low, but will increase if the concentration of the photosensitizer in the hypoxic tissue is increased. Attempting to do so simply by increasing the dose of photosensitizer that is administered may produce too high a concentration in vital non-malignant tissues. However, if the photosensitizer had a significant degree of affinity or specificity for hypoxic tissues, it would accumulate preferentially in such tissues.

Thus, there is a need for better photochemotherapeutic agents that are cleared rapidly from normal tissues and especially skin, and ones that are effective in the hypoxic areas of tumors.

OBJECT OF INVENTION

It is, therefore, an object of the present invention to provide novel photochemotherapeutic agents of the porphyrin and chlorin type substituted with hydroxylated residues via amide bonds, which are good tissue photosensitizers, accumulate preferentially in malignant tissues, especially in necrotic and/or hypoxic areas, show low systemic toxicity, clear rapidly from skin and most other normal tissues.

Another object is to provide chemotherapeutic agents of the above type which exhibit at least some degree of anti-tumor activity even in the dark.

BRIEF STATEMENT OF THE INVENTION

By one aspect, of this invention there are provided compounds of the formula $$(ZNHCO)_n X$$

wherein:

Z is selected from mono-, di-, and polyhydroxyalkyl residues with the provisio that Z does not include a carboxyl group;

X is selected from substituted tetrapyrroles in which the substituent is at least one of the group consisting of methyl, ethyl, vinyl, hydroxyethyl, alkoxyethyl, methylcarboxy, ethylcarboxy, Z-substituted propylamide, phenyl and $(ZNHCO)_n$-substituted phenylamide, and n is an integer from 1 to 8.

In a preferred aspect of this invention the tetrapyrrole is either derived by various procedures from naturally-occurring tetrapyrroles or synthesized by coupling of suitably substituted pyrroles and benzaldehydes. These cyclic tetrapyrroles have the following basic ring structure

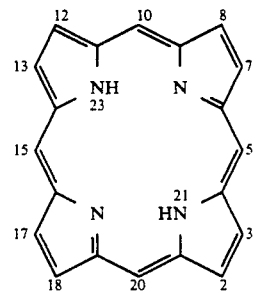

and also include perhydro-, e.g., dihydro- and tetrahydro-derivatives of the said ring structure.

By another aspect of this invention, there is provided a method for detection and treatment of malignant tissue abnormalties in a patient comprising administering to said patient an effective amount of tetrapyrrole derivatives of amino alcohols described herein before and exposing said tissue abnormality to light within the photoactivating spectrum of said tetrapyrrole derivatives.

DETAILED DESCRIPTION OF PREFERRED EMBODIMENTS

The compounds of the present invention are designated as derivatives of the tetrapyrrole for convenience. Hence, the terms "tetrapyrrole" and "porphyrin" are used here to designate compounds of the cyclic structure shown herein before and their corresponding perhydro derivatives. Another characteristic of the present new compounds is that they all bear at least one residue which includes one amide bond by which an hydroxylated residue is linked to the tetrapyrrole part.

Thus, the present invention concerns porphyrin or perhydroporphyrin derivatives of amino alcohols, in which the porphyrin chromophore and the hydroxylated residues are linked by amide bonds. This amide bond involves the amino group of the amino alcohol and a carboxyl group attached to the porphyrin.

The tetrapyrroles employed in the present invention to form the aforesaid amide bond include two major classes which are both well-known to those skilled in the art, i.e. 1) the carboxy-containing tetrapyrroles and their perhydro analogues derived by various means from natural porphyrins and 2) the carboxy-containing meso-tetraphenylporphins and their perhydroanalogues. Exemplary tetrapyrroles valuable for the preparation of the compounds contemplated by the present invention are listed in Table I.

The amino alcohols employed in the present invention to form the aforesaid amide bond include mono-, di- or polyhydroxylated acyclic or cyclic, primary or secondary amines. Hence, these amino alcohols show three characteristics: 1) they contain, of course, at least one hydroxyl group; 2) they

TABLE I

| Tetrapyrrole | 2 | 3 | 5 | 7 | 8 | 10 | 12 | 13 | 15 | 17 | 18 | 20 |
|---|---|---|---|---|---|---|---|---|---|---|---|---|
| Coproporphyrin I | PO | Me | H | PO | Me | H | PO | Me | H | PO | Me | H |
| Coproporphyrin III | PO | Me | H | PO | Me | H | PO | Me | H | Me | PO | H |
| Deuteroporphyrin IX | PO | Me | H | Me | H | H | Me | H | H | Me | PO | H |
| Hematoporphyrin IX | PO | Me | H | EO | Me | H | EO | Me | H | Me | PO | H |
| Hematoporphyrin IX dialkylethers | PO | Me | H | EOE | Me | H | EOE | Me | H | Me | PO | H |
| Mesoporphyrin IX | PO | Me | H | Et | Me | H | Et | Me | H | Me | PO | H |
| Protoporphyrin IX | PO | Me | H | V | Me | H | V | Me | H | Me | PO | H |
| Uroporphyrin IX | PO | AO | H | PO | AO | H | PO | AO | H | AO | PO | H |
| Chlorine$_6$ (16–17-dihydro) | CO | Me | H | Et | Me | H | V | Me | H | Me, H | PO, H | H |
| Pentacarboxyporphyrin I | PO | Me | H | PO | Me | H | PO | Me | H | PO | AO | H |
| Pentacarboxyporphyrin III | PO | Me | H | PO | Me | H | PO | Me | H | AO | PO | H |
| Hexacarboxyporphyrin I | PO | Me | H | PO | AO | H | PO | Me | H | PO | AO | H |
| Hexacarboxyporphyrin III | PO | Me | H | PO | Me | H | PO | AO | H | PO | AO | H |
| Heptacarboxyporphyrin I | PO | Me | H | PO | AO | H | PO | AO | H | PO | AO | H |
| Tetracarboxyphenylporphyrin | H | H | φ-CO | H | H | φ-CO | H | H | φ-CO | H | H | φ-CO |
| Tricarboxyphenyl-phenylporphin | H | H | φ-CO | H | H | φ-CO | H | H | φ-CO | H | H | φ |
| Dicarboxyphenyl-diphenylporphin-S | H | H | φ-CO | H | H | φ | H | H | φ-CO | H | H | φ |
| Dicarboxyphenyl-diphenylporphin-A | H | H | φ-CO | H | H | φ-CO | H | H | φ | H | H | φ |
| Carboxyphenyl-triphenylporphin | H | H | φ-CO | H | H | φ | H | H | φ | H | H | φ |

CO = —CO$_2$H
AO = —CH$_2$CO$_2$H
PO = —CH$_2$CH$_2$CO$_2$H
EO = —CH(OH)CH$_3$
EOE = —CH(OR)CH$_3$, wherein R = alkyl
Me = —CH$_3$
Et = —CH$_2$CH$_3$
V = —CH=CH$_2$
φ = Benzene ring do not contain a carboxyl group; 3) their amino group is available to form the aforesaid amide bond with a carboxyl group of the selected tetrapyrrole. Thus, various amino alcohols are valuable for the present invention including 2-aminoethanol, 2-amino-1,3-propanediol, 2-amino-2-(hydroxymethyl)-1,3-propanediol, D-glucosamine and similar such amino alcohols.

Preferred compounds may be derived from commercially available tetrapyrroles selected from hematoporphyrin IX dihydrochloride, mesoporphyrin IX dihydrochloride, protoporphyrin IX dihydrochloride or deuteroporphyrin IX dimethylester. Hence, the preferred tetrapyrroles from which the new compounds are derived are those wherein at least two carboxyl groups or lower alkyl esters are present in the tetrapyrrole, preferably asymmetrically attached to the porphyrin ring system. These preferred tetrapyrroles are represented by the formula

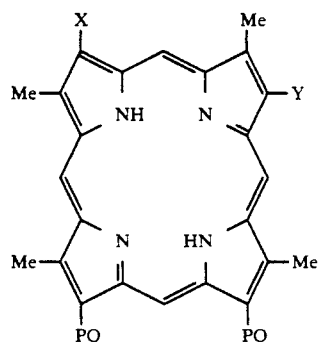

wherein
Me: methyl
X: H, vinyl, ethyl, acetyl, formyl, hydroxyethyl, alkoxyethyl
Y: H, vinyl, ethyl, acetyl, formyl, hydroxyethyl, alkoxyethyl
PO: propionic acid The present new compounds are prepared by usual amidification procedures between the selected amino alcohol and the carboxyl containing tetrapyrrole. These procedures are well known to those skilled in the art. They involve any amide-forming derivative of the tetrapyrrole carboxylic acid, e.g. lower alkyl esters, activated esters, acyl chlorides, anhydrides and mixed anhydrides.

The preferred preparative procedures use lower alkyl ester and activated (trifluoro acetate) ester. The reactants are mixed, in a suitable solvent when necessary. Heating up to 90° C. can be used. Examples of detailed procedures are to be found below. Unreacted tetrapyrrole and side-products are separated from the amide derivatives by chromatographic techniques and crystallization.

Agents valuable for photodetection or phototherapy should have the following properties 1) be non-toxic, in the dark, to normal tissue, at dosage requested for photodetection or phototherapy;

2) accumulate selectively within neoplastic tissue, i.e. clear rapidly from normal tissue and be retained by malignant tissue;

3) emit detectable fluorescence when illuminated with light (photodetection);

4) be photoactivated by illumination with light in the red spectral region and deactivate by a process that exert a cell killing effect (phototherapy).

The new compounds of this invention show all the properties listed herein before and present an improvement relative to other porphyrins actually used for photodynamic therapy.

The present compounds are apparently non-toxic at therapeutic dosages. Dosage levels up to 100 mg/kg body weight caused no mortality of test animals.

It has been shown by various methods that the compounds contemplated by the present invention accumulate selectively within the tumors. In vivo pharmacokinetics experiments monitored with fluorescence equipment demonstrate that, at any time after administration of the compounds to test animals, the malignant tissues fluoresce at least twice as much as the normal tissue, this fluorescence being typical of the present compounds. When the animals were sacrificed, all of the compounds tested showed strong fluorescence in the tumor with no fluorescence in the adjacent healthy tissue as well as in the skin, bowel, skeletal muscle, lungs, heart, thymus, liver, spleen or kidneys. Of all the organs observed only the pancreas showed significant but low fluorescence intensity.

The present compounds can be photoactivated by illumination with light in the red spectral region so as to exert a cell killing effect. This property has been shown by in vitro as well as in vivo experiments.

Hemolysis of erythrocytes upon irradiation in the presence of a photosensitizer is a method used by those skilled in the art to test the potency of photosensitizing agents to cause the death of cells by irradiation. Experiments made according to the said technique with the present compounds demonstrate that they produce higher level of photohemolysis, at lower dose, than the compounds actually used for photodynamic therapy.

Experiments were conducted in mice transplanted with a carcinoma. The present compounds were administered to the mice and the region of the tumor was irradiated with light of wavelength greater than 600 nm. Several days after exposure to the photoactivating light, there was no evidence of residual tumor.

An interesting property of the present compounds is their strong tendency to accumulate preferentially in the necrotic and/or hypoxic areas of malignant tissues, as demonstrated by fluorescence in vivo experiments on test animals bearing carcinomas.

It has been found that compounds of the present invention show a strong tendency to accumulate preferentially in the necrotic and/or hypoxic areas of malignant tissues. Thus, it is reasonable to expect that such photosensitizers are preferentially effective against hypoxic cells and thus, under appropriate circumstances, may be an adjunct to radiation therapy or chemotherapy for local control of malignant tumors that otherwise would be incurable. For example, squamous cell carcinomas of the head and neck, which usually contain a relatively high percentage of necrotic material may be treated. Such cancers usually respond poorly to chemotherapy, and they sometimes recur even after treatment with a tissue tolerance dose (maximum safe dose) of ionizing radiation. Since cancers of this type are quite common, even a small improvement in the local control rate would be of benefit to a significant number of patients.

Phototoxic damage to hypoxic tissue can be increased either by increasing the tissue concentration of oxygen or by increasing the concentration of photosensitizer. The former is not very effective but as the photosensitizers of the present invention tend to accumulate in necrotic/hypoxic tissue they selectively increase the intensity of the phototoxic reaction in such tissues.

EXAMPLE 1

Synthesis of Mesoporphyrin IX di(2-hydroxyethylamide) (acyl chloride method)

0.3 mL of oxalyl chloride was added dropwise to a suspension of 100 mg of mesoporphyrin IX dihydrochloride in 5 mL of dry dichloromethane heated under reflux and the heating was maintained for 20 min. The solvent was distilled under reduced pressure to give mesoporphyrin IX di(acyl chloride) which was used without further purification for the following step.

5mL of dry dichloromethane was added to the di(acyl chloride) residue and the mixture was heated under reflux during the addition of 0.5 mL of 2-aminoethanol. After refluxing the mixture for 1 h, another 0.5 mL of 2-aminoethanol was added to the mixture and the heating was maintained for another 1 h. After distillation of the solvent under reduced pressure, the residue was taken up in 20 mL of ethanol and the precipitate was collected by centrifugation. The precipitate was taken up in ethanol and centrifugated three more times. The final precipitate was washed three times with ethyl ether and dried under reduced pressure. This procedure gave 73 mg of mesoporphyrin-IX di(2-hydroxyethylamide) as purple crystals.

IUPAC name: 7,12-diethyl-3,8,13,17-tetramethyl-2,18-bis [2-(N-(2-hydroxyethyl)carbamoyl)ethyl]-21H, 23H-porphin Melting point 310°–311° C. dec.

IR $\nu$ kBr in cm$^{-1}$ 3500–3200 (O-H), 3310 (N-H), 2955, 2925, 2860, 1640 (C=O, amide I band), 1550 (amide II band), 1110, 1065, 840.

NMR $\delta$ DMSO$_{d6}$ in ppm 10.35–10.25 (4 s, 4H, H-5, 10, 15, 20), 8.03 (t, J=6.0 Hz, 2H, NH amide), 4.35 (t, J=6.0 Hz, 4H COC$\underline{H_2}$CH$_2$-2, 18), 4.12 (bq, J=7.5 Hz, 4H, C$\underline{H_3}$CH$_2$-7, 12), 3.64 (4 s, 12H, CH$_3$-3, 8, 13, 17), 3.24 (t, J=6.0 Hz, 4H, COCH$_2$C$\underline{H_2}$-2, 18), 3.12–3.07 (2t, J=6.0 Hz, 4H, NHC$\underline{H_2}$CH$_2$ OH and 4H, NHCH$_2$C$\underline{H_2}$OH), 1.83 (t, J=7.5 Hz, C$\underline{H_3}$CH$_2$-7, 12), −4.0 (s, 2H, NH-21, 23).

EXAMPLE 2

Synthesis of Mesoporphyrin IX di(2-hydroxyethylamide) (mixed anhydride method)

0.4 mL of triethylamine was added to a suspension of 300 mg of mesoporphyrin IX dihydrochloride in 30 mL of tetrahydrofuran. The suspension was stirred for 15 min., 0.4 mL of ethyl chloroformate was added and the mixture was stirred for another 15 min. A solution of 0.5 mL of 2-aminoethanol in 10 mL of tetrahydrofuran was added to the mixture which was stirred for 2 h under slight heating (~50° C.). The solvent was distilled under reduced pressure and the residue was taken up in 50 mL of ethanol. The precipitate was collected by centrifugation and treated as described in Example 1 to afford 240 mg of mesoporphyrin IX di(2-hydroxyethylamide) with properties identical to those described in Example 1.

EXAMPLE 3

Synthesis of Mesoporphyrin IX di(2-hydroxyethylamide) (lower ester method)

1.5 mL of concentrated sulfuric acid was added to a solution of 250 mg of mesoporphyrin IX dihydrochloride in 30 mL of absolute ethanol and the mixture was heated under reflux for 3 h. The mixture was cooled and 250 mL of chloroform was added. The layers separated and the organic layer was washed several times with water, brine and then dried over anhydrous sodium sulfate. The solvent was distilled under reduced pressure and the residue was chromatographed on deactivated silica gel with mixtures of petroleum ether-ethyl ether. The main colored fraction was mesoporphyrin IX di(ethylester) which was used for the following step without further purification.

10 mL of 2-aminoethanol was added to the mesoporphyrin IX di(ethylester) and the solution was heated at 110° C. for 2 h. The mixture was cooled, 40 mL of ethanol was added and the suspension was centrifugated. The precipitate was treated as described in Example 1 to afford 204 mg of mesoporphyrin IX di(2-hydroxyethylamide) with properties identical to those described in Example 1.

EXAMPLE 4

Synthesis of Hematoporphyrin IX 8,13-di(methylether) di(ethanolamide)

2.5 mL of concentrated sulfuric acid was added to a solution of 1 g of hematoporphyrin IX dihydrochloride in 50 mL of dry methanol and the mixture was heated under reflux with stirring for 5 h. The mixture was cooled and 250 mL of chloroform was added. The layers were separated and the organic layer was washed with water, brine and then dried over anhydrous sodium sulfate. The solvent was distilled under reduced pressure and the residue was chromatographed or deactivated silica gel with ethyl ether. The main colored fraction is hematoporphyrin IX 8,13-di(methylether) di(methylester) which was used for the following step without further purification.

A mixture of 20 mL of dioxane and 10 mL of 2-aminoethanol was added to the hematoporphyrin IX di(alkylether) di(alkylester) prepared above and the solution was heated under reflux for 2 h. The dioxane was distilled and the mixture was heated at 110° C. for another 10 min. The mixture was cooled and neutralized with 6M aqueous hydrochloric acid. Chloroform was added, the layers were separated and the organic layer was treated as described above. The residue was chromatographed on silica gel with chloroform-methanol mixtures. The second colored fraction contained the diamide derivative. This product was dissolved in a small volume of ethanol and precipitated by adding a petroleum ether-ethyl ether (1:3) mixture. This procedure gave, after drying at 80° C. for 7 h under reduced pressure, 800 mg of hematoporphyrin IX 8,13-di(methylether) di(ethanolamide) as a purple powder.

IUPAC name: 8,13-bis(1-methoxyethyl)-3,7,12,17-tetramethyl-2,18-bis[2-(N-(2-hydroxyethyl)carbamoyl) ethyl]-21H,23H-porphin Melting point 118°–119° C.

IR $\nu$ KBr in cm$^{-1}$ 3500–3200 (O-H), 3300 (N-H), 2955, 2925, 2860, 1640 (C=O, amide I band), 1545 (amide II band), 1105, 1070, 840.

NMR $\delta$ CDCl$_3$ in ppm 10.60–10.07 (4 s, 4H, H-5, 10, 15, 20), 6.68 (bm, 2H, NH amide), 6.04 (q, J=6.5 Hz, 2H, CH$_3$C(OMe)H-8, 13), 4.37 (bt, J=7.0 Hz, 4H, COC$\underline{H_2}$CH$_2$-2, 18), 3.70–3.69 (2 s, 6H, 2 C$\underline{H_3}$O), 3.66–3.62 (4 s, 12H, CH$_3$-3, 7, 12, 17), 3.07 (t, J=7.0 Hz, 4H, COCH$_2$C$\underline{H_2}$-2, 18), 2.95 (bt, 4H, NHCH$_2$C$\underline{H_2}$OH), 2.78 (bm, 4H, NHC$\underline{H_2}$CH$_2$OH), 2.24 (d, J=6.5 Hz, 2H, C$\underline{H_3}$ C(OMe)H-8, 13), −3.90 (s, 2H, NH-21, 23).

EXAMPLE 5

Synthesis of Hematoporphyrin IX 8,13-di(ethylether) di(ethanolamide)

1 g of hematoporphyrin IX dihydrochloride was first reacted with 50 mL of dry ethanol to give hematoporphyrin IX 8,13-di(ethylether) di(ethylester) according to the process of Example 4. This product was then treated with 2-aminoethanol in dioxane to give 795 mg of hematoporphyrin IX 8,13-di(ethylether) di(ethanolamide) as purple powder.

IUPAC name: 8,13-bis(1-ethoxyethyl-3,7,12,17-tetramethyl-2,18-bis[2-(N-2-hydroxyethyl)carbamoyl)ethyl]-21H,23H-porphin Melting point 128°–129° C.

IR ν KBr in cm$^{-1}$ 3500–3200 (O-H), 3310 (N-H), 2960, 2925, 2860, 1640 (C=O, amide I band), 1540 (amide II band), 1100, 1065, 840.

NMR δ CDCl$_3$ in ppm 10.70–10.11 (4 s, 4H, H-5, 10, 15, 20), 6.68 (bm, 2H, NH amide), 6.13 (q, J=6.5 Hz, 2H, CH$_3$C(OEt)H-8, 13), 4.42 (bt, 4H, COCH$_2$CH$_2$-2, 18), 3.81 (q, J=7.0 Hz, 4H, 2 CH$_3$CH$_2$O), 3.69 (4 s, 12H, CH$_3$-3, 7, 12, 17), 3.04 (bt, 4H, COCH$_2$CH$_2$-2, 18), 2.85 (bm, 4H, NHCH$_2$CH$_2$OH), 2.73 (bm, 4H, NHCH$_2$CH$_2$OH), 2.24 (d, J=6.5 Hz, 6H, CH$_3$C(OEt)H-8, 13), 1.39 (t, J=7.0 Hz, 6H, 2 CH$_3$CH$_2$O), −3.90 (bs, 2H, NH-21, 23).

EXAMPLE 6

Synthesis of Hematoporphyrin IX 8,13-di(propylether) di(ethanolamide)

1 g of hematoporphyrin IX dihydrochloride was first reacted with 50 mL of dry propanol at 90° C. to give hematoporphyrin IX 8,13-dipropylether) di(propylester) according to the process of Example 4. This product was then treated with 2-aminoethanol in dioxane to give 870 mg of hematoporphyrin IX 8,13-di(propylether) di(ethanolamide) as purple powder.

IUPAC name: 8,13-bis(1-propoxyethyl)-3,7,12,17-tetra methyl-2,18-bis[2-(N-(2-hydroxyethyl)carbamoyl)ethyl]-21H,23H-porphin Melting point 139°–140° C.

IR ν KBr in cm$^{-1}$ 3500–3200 (O-H), 3310 (N-H), 2955, 2925, 2860, 1640 (C=O, amide I band), 1540(amide II band), 1090, 1070, 840.

NMR δ CDCl$_3$ in ppm 10.66–9.98 (4 s, 4H, H-5, 10, 15, 20), 6.70 bm, 2H, NH amide), 6.08 (q, J=6.5 Hz, 2H, CH$_3$C(OPr)CH-8, 13), 4.28 (bt, J=7.0 Hz, 4H, COCH$_2$CH$_2$-2, 18), 3.65–3.51 (4 s, 16H, CH$_3$-3, 7, 12, 17 and 2 CH$_3$CH$_2$CH$_2$O), 3.00 (q, 4H, J=7.0 Hz, COCH$_2$CH$_2$-2, 18), 2.90 (bm, 4H, NHCH$_2$CH$_2$OH), 2.74 (bm, 4H, NHCH$_2$CH$_2$OH), 2.22 (d, J=6.5 Hz, 6H, CH$_3$C(OPr)CH-8, 13), 1.79 (sext, J=7.0 Hz, 4H, 2 CH$_3$CH$_2$CH$_2$O), 0.93 (t, J=7.0 Hz, 6H, 2 CH$_3$CH$_2$CH$_2$O), 3.90 (s, 2H, NH −21, 23).

EXAMPLE 7

Synthesis of Hematoporphyrin IX 8,13-di(butylether) di(ethanolamide)

1 g of hematoporphyrin IX dihydrochloride was first reacted with 50 mL of dry butanol at 90° C. to give hematoporphyrin IX 8,13-di(butylether) di(butylester) according to the process of Example 4. This product was then treated with 2-aminoethanol in dioxane to give 830 mg of hematoporphyrin IX 8,13-di(butylether) di(ethanolamide) as purple powder.

IUPAC name: 8,13-bis(1-butoxyethyl)-3,7,12,17-tetramethyl-2,18-bis[2-(N-(2-hydroxyethyl)carbamoyl)ethyl]-21H,23H-porphin Melting point 157°–158° C.

IR ν KBr in cm$^{-1}$ 3500–3200 (O-H), 3310 (N-H), 2955, 2925, 2860, 1640 (C=O, amide I band), 1545 (amide II band), 1100, 1070, 840.

NMR δ CDCl$_3$ in ppm 10.67–10.12 (4 s, 4H, H-5, 10, 15, 20), 6.68 (bm, 2H, NH amide), 6.09 (q, J=6.5 Hz, 2H, CH$_3$C(OBu)H-8, 13), 4.41 (bm, 4H, COCH$_2$ CH$_2$-2, 18), 3.74 (t, J=6.5 Hz, 4H, 2 CH$_3$CH$_2$ CH$_2$CH$_2$O), 3.72–3.60 (s, 12H, CH$_3$-3, 7, 12, 17), 3.11 (bt, 4H, COCH$_2$CH$_2$-2, 18), 2.97 (bm, 4H, NHCH$_2$CH$_2$OH), 2.73 (bm, 4H, NHCH$_2$CH$_2$OH), 2.23 (d, J=6.5 Hz, 6H, CH$_3$C(OBu)H-8, 13), 1.76 (b, quint, J=6.5 Hz, 4H, 2 CH$_3$CH$_2$ CH$_2$CH$_2$O), 1.45 (bm, 4H, 2 CH$_3$CH$_2$CH$_2$CH$_2$O), 0.84 (t, J=6.5 Hz, 6H, 2 CH$_3$CH$_2$CH$_2$CH$_2$O), −3.92 (s, 2H, NH-21, 23).

EXAMPLE 8

Synthesis of Hematoporphyrin IX 8,13-di(isobutylether) di(ethanolamide)

1 g of hematoporphyrin IX dihydrochloride was first reacted with 50 mL of dry isobutanol at 90° C. to give hematoporphyrin IX 8,13-di(isobutylether) di(isobutylester) according to the process of Example 4. This product was then treated with 2-aminoethanol in dioxane to give 840 mg of hematoporphyrin IX 8, 13-di(isobutylether) di(ethanolamide) as purple powder.

IUPAC name: 8,13-bis(1-isobutoxyethyl)-3,7,12,17-tetramethyl-2,18-bis[2-(N-(2-hydroxyethyl)carbamoyl)ethyl]-21H,23H-porphin Melting point 165°–166° C.

IR ν KBr in cm$^{-1}$ 3500–3200 (O-H), 3310 (N-H), 2955, 2925, 2860, 1640 (C=O, amide I band), 1540 (amide II band), 1085, 1065, 840.

NMR δ CDCl$_3$ in ppm 10.68–10.08 (4 s, 4H, H-5, 10, 15, 20), 6.68 (bm, 2H, NH amide), 6.08 (q, J=6.5 Hz, 2H, CH$_3$C(OiBu)H-8, 13), 4.38 (q, J=6.5 Hz, 4H, COCH$_2$CH$_2$-2, 18), 3.70–3.40 (s and d, 16H, CH$_3$-3, 7, 12, 17 and 2 (CH$_3$)$_2$CHCH$_2$O), 3.08 (q, J=6.5 Hz, 4H, COCH$_2$CH$_2$-2, 18), 2.94 (bm, 4H, NHCH$_2$CH$_2$OH), 2.72 (bm, 4H, NHCH$_2$CH$_2$OH), 2.28 (d, J=6.5 Hz, 6H, CH$_3$C(iOBu)H-8, 13), 2.12 (m, J=6.5 Hz, 2H, 2 (CH$_3$)$_2$CHCH$_2$O), 0.98 (d, J=6.5 Hz, 6H, 2 (CH$_3$)$_2$CHCH$_2$O), −3.83 (s, 2H, NH-21, 23).

EXAMPLE 9

Synthesis of Deuteroporphyrin IX di(ethanolamide)

200 mg of deuteroporphyrin IX dihydrochloride was first reacted with 30 mL of dry ethanol to give deuteroporphyrin IX di(ethylester) according to the process of Example 3. This product was then treated with 2-aminoethanol to produce 170 mg of deuteroporphyrin IX di(ethanolamide) as red crystals.

IUPAC name: 3,7,12,17-tetramethyl-2,18-bis[2-(N-(2-hydroxyethyl)carbamoyl)ethyl]-21H,23H-porphin Melting point >350° C. dec.

IR ν KBr in cm$^{-1}$ 3500–3200 (O-H), 3310 (N-H), 2955, 2925, 2860, 1640 (C=O, amide I band), 1545 (amide II band), 1050, 840.

NMR δ DMSO$_{d6}$ in ppm 10.31–10.28 (4 s, 4H, H-5, 10, 15, 20), 9.32 (s, 2H, H-8, 13), 8.02 (bt, J=6.0 Hz, 2H, NH amide), 4.36 (t, J=6.0 Hz, 4H, COCH$_2$CH$_2$-2, 18), 3.80–3.60 (4 s, 12H, CH$_3$-3, 7, 12, 17), 3.24 (bt, J=6.0 Hz, 4H, COCH$_2$CH$_2$-2, 18), 3.22–3.17 (2t, J=6.0 Hz, 8H, NHCH$_2$ CH$_2$OH and NHCH$_2$CH$_2$OH), −4.01 (s, 2H, NH-21, 23).

EXAMPLE 10

Synthesis of Mesoporphyrin IX di(bis(hydroxymethyl)methanamide) (activated ester method)

250 mg of mesoporphyrin IX dihydrochloride was dissolved in 20 mL of 2,2,2-trifluoroethanol. The solution was saturated with gaseous hydrochloric acid and allowed to stand in the dark for 24 h. 10 mL of benzene was added and the mixture was evaporated to dryness under reduced pressure, producing mesoporphyrin IX di(2,2,2-trifluoroethylester), which was used for the next step without further purification.

The activated diester was dissolved in 15 mL of dimethylformamide and the solution was heated to 90° C. 500 mg of 2-amino-1,3-propanediol hydrochloride and 2 mL of triethylamine were added and the heating was maintained for 3 h. The mixture was cooled in ice, vacuum filtered to remove excess amine and evaporated to dryness. The residue was taken up in a small volume of methanol and 80 mL of 2% aqueous sodium bicarbonate was added. The precipitate was collected by centrifugation, dissolved in a small volume of ethanol, precipitated once more by adding 80 mL of ethyl ether. This precipitation procedure was repeated twice. The final product was dried at 80° C. under reduced pressure producing 210 mg of mesoporphyrin IX di(bis(hydroxymethyl)methanamide) as brownish crystals.

IUPAC name: 7,12-diethyl-3,8,13,17-tetramethyl-2,18-bis[2-(N-(1, 3-dihydroxy-2-propyl)carbamoyl)ethyl]-21H,23H-porphin Melting point >350° C. dec.

IR $\nu$ KBr in cm$^{-1}$ 3500–3200 (O-H), 3310 (N-H), 2955, 2925, 2860, 1640 (C=O, amide I band), 1550 (amide II band), 1100, 1050, 840.

NMR $\delta$ DMSO$_{d6}$ in ppm 10.34–10.10 (4 s, 4H, H-5, 10, 15, 20), 7.85 (m, 2H, NH amide), 4.37 (bt, 4H, COC$\underline{H_2}$CH$_2$-2, 18), 4.10 (bq, J=7.5 Hz, 4H, CH$_3$C$\underline{H_2}$-7, 12), 3.65 (4 s, 12H, CH$_3$-3, 8, 13, 17), 3.30 (bm, 12H, 2 NHCH(C$\underline{H_2}$OH)$_2$ and COCH$_2$C$\underline{H_2}$-2, 18), 3.12 (bm, 2H,2 NHC$\underline{H}$CH$_2$OH)$_2$), 1.82 (bt, 6H, C$\underline{H_3}$CH$_2$-7, 12).

EXAMPLE 11

Synthesis of Mesoporphyrin IX di(tris(hydroxymethyl)methanamide) (activated ester method)

250 mg of mesoporphyrin IX dihydrochloride was reacted with 2,2,2-trifluoroethanol to produce the di(2,2,2-trifluoroethylester) according to the process of Example 10. This activated ester was reacted with 500 mg of 2-amino-2-(hydroxymethyl)-1,3-propanediol to produce 215 mg of mesoporphyrin IX di(tris(hydroxymethyl)methanamide) as brownish crystals.

IUPAC name: 7,12-diethyl-3,8,13,17-tetramethyl-2,18-bis[2-(N-(1,3-dihydroxy-2-hydroxymethyl-2propyl)carbamoyl)ethyl]-21H,23H-porphin Melting point >350° C. dec.

IR $\nu$ KBr in cm$^{-1}$ 3500–3200 (O-H), 3310 (N-H), 2955, 2925, 2860, 1640 (C=O, amide I band), 1555 (amide II band), 1050, 1040, 840.

NMR $\delta$ DMSO$_{d6}$ in ppm 10.30–10.10 (4 s, 4H, H-5, 10, 15, 20), 7.95 (m, 2H, amide), 4.34 (bt, 4H, COC$\underline{H_2}$CH$_2$-2, 18), 4.12 (bq, 4H, CH$_3$C$\underline{H_2}$-7, 12), 3.7–3.3 (bs, 28H, CH$_3$-3, 8, 13, 17; COC$\underline{H_2}$C$\underline{H_2}$-2, 18 and 2 NHC(C$\underline{H_2}$OH)$_3$), 1.83 (t, J=7.5 Hz, 6H, C$\underline{H_3}$CH$_2$-7, 12).

Using the methods described in Examples 1 to 11 and tetrapyrrole compounds either commercially available or easily prepared from commercially available compounds by those skilled in the art, the following preferred compounds of this invention can be synthesized:

Coproporphyrin I mono(ethanolamide)
Coproporphyrin I di(ethanolamide)
Coproporphyrin I mono(bis(hydroxymethyl)methanamide)
Coproporphyrin I di(bis(hydroxymethyl)methanamide)
Coproporphyrin I mono(tris(hydroxymethyl)methanamide)
Coproporphyrin I di(tris(hydroxymethyl)methanamide)
Coproporphyrin I mono(D-glucosamide)
Coproporphyrin I di(D-gluosamide)
Coproporphyrin III mono(ethanolamide)
Coproporphyrin III di(ethanolamide)
Coproporphyrin III mono(bis(hydroxymethyl)methanamide)
Coproporphyrin III di(bis(hydroxymethyl)methanamide)
Coproporphyrin III mono(tris(hydroxymethyl)methanamide)
Coproporphyrin III di(tris(hydroxymethyl)methanamide)
Coproporphyrin III mono(D-gluosamide)
Coproporphyrin III di(D-gluosamide)
Deuteroporphyrin IX di(ethanolamide)
Deuteroporphyrin IX mono(bis(hydroxymethyl)methanamide)
Deuteroporphyrin IX di(bis(hydroxymethyl)methanamide)
Deuteroporphyrin IX mono(tris(hydroxymethyl)methanamide)
Deuteroporphyrin IX di(tris(hydroxymethyl)methanamide)
Deuteroporphyrin IX mono(D-gluosamide)
Deuteroporphyrin IX di(D-gluosamide)
Hematoporphyrin IX mono(ethanolamide)
Hematoporphyrin IX di(ethanolamide)
Hematoporphyrin IX mono(bis(hydroxymethyl)methanamide)
Hematoporphyrin IX di(bis(hydroxymethyl)methanamide)
Hematoporphyrin IX di(bis(hydroxymethyl)methanamide)
Hematoporphyrin IX mono(tris(hydroxymethyl)methanamide)
Hematoporphyrin IX di(tris(hydroxymethyl)methanamide)
Hematoporphyrin IX mono(D-gluosamide)
Hematoporphyrin IX di(D-gluosamide)
Hematoporphyrin IX 8,13-di(alkylether) mono(ethanolamide)
Hematoporphyrin IX 8,13-di(alkylether) di(ethanolamide)
Hematoporphyrin IX 8,13-di(alkylether) mono(bis(hydroxymethyl)methanamide)
Hematoporphyrin IX 8,13-di(alkylether) di(bis(hydroxymethyl) methanamide)
Hematoporphyrin IX 8,13-di(alkylether) mono(tris(hydroxymethyl)methanamide)
Hematoporphyrin IX 8,13-di(alkylether) di(tris(hydroxymethyl)methanamide)
Hematoporphyrin IX 8,13-di(alkylether) mono(D-gluosamide)
Hematoporphyrin IX 8,13-di(alkylether) di(D-gluosamide)
Mesoporphyrin IX mono(ethanolamide)
Mesoporphyrin IX di(ethanolamide)
Mesoporphyrin IX mono(bis(hydroxymethyl)methanamide)
Mesoporphyrin IX di(bis(hydroxymethyl)methanamide)
Mesoporphyrin IX mono(tris(hydroxymethyl)methanamide)
Mesoporphyrin IX di(tris(hydroxymethyl)methanamide)
Mesoporphyrin IX mono(D-gluosamide)
Mesoporphyrin IX di(D-gluosamide)
Protoporphyrin IX mono(ethanolamide)

Protoporphyrin IX di(ethanolamide)
Protoporphyrin IX mono(bis(hydroxymethyl)methanamide)
Protoporphyrin IX di(bis(hydroxymethyl)methanamide)
Protoporphyrin IX mono(tris(hydroxymethyl)methanamide)
Protoporphyrin IX di(tris(hydroxymethyl)methanamide)
Protoporphyrin IX mono(D-gluosamide)
Protoporphyrin IX di(D-gluosamide)
Chlorin $e_6$ mono(ethanolamide)
Chlorin $e_6$ di(ethanolamide)
Chlorin $e_6$ tri(ethanolamide)
Chlorin $e_6$ mono(bis(hydroxymethyl)methanamide)
Chlorin $e_6$ di(bis(hydroxymethyl)methanamide)
Chlorin $e_6$ tri(bis(hydroxymethyl)methanamide)
Chlorin $e_6$ mono(tris(hydroxymethyl)methanamide)
Chlorin $e_6$ di(tris(hydroxymethyl)methanamide)
Chlorin $e_6$ tri(hydroxymethyl)methanamide)
Chlorin $e_6$ mono(D-gluosamide)
Chlorin $e_6$ di(D-gluosamide)
Chlorin $e_6$ tri(D-gluosamide)
Uroporphyrin IX mono(ethanolamide)
Uroporphyrin IX di(ethanolamide)
Uroporphyrin IX poly(ethanolamide)
Uroporphyrin IX mono(bis(hydroxymethyl)methanamide)
Uroporphyrin IX di(bis(hydroxymethyl)methanamide)
Uroporphyrin IX poly(bis(hydroxymethyl)methanamide)
Uroporphyrin IX mono(tris(hydroxymethyl)methanamide)
Uroporphyrin IX di(tris(hydroxymethyl)methanamide)
Uroporphyrin IX poly(tris(hydroxymethyl)methanamide)
Uroporphyrin IX mono(D-gluosamide)
Uroporphyrin IX di(D-gluosamide)
Uroporphyrin IX poly(D-gluosamide)
Pentacarboxy I mono(ethanolamide)
Pentacarboxy I di(ethanolamide)
Pentacarboxy I poly(ethanolamide)
Pentacarboxy I mono(bis(hydroxymethyl)methanamide)
Pentacarboxy I di(bis(hydroxymethyl)methanamide)
Pentacarboxy I poly(bis(hydroxymethyl)methanamide)
Pentacarboxy I mono(tris(hydroxymethyl)methanamide)
Pentacarboxy I di(tris(hydroxymethyl)methanamide)
Pentacarboxy I poly(tris(hydroxymethyl)methanamide)
Pentacarboxy I mono(D-gluosamide)
Pentacarboxy I di(D-gluosamide)
Pentacarboxy I poly(D-gluosamide)
Pentacarboxy III mono(ethanolamide)
Pentacarboxy III di(ethanolamide)
Pentacarboxy III poly(ethanolamide)
Pentacarboxy III mono(bis(hydroxymethyl)methanamide)
Pentacarboxy III di(bis(hydroxymethyl)methanamide)
Pentacarboxy III poly(bis(hydroxymethyl)methanamide)
Pentacarboxy III mono(tris(hydroxymethyl)methanamide)
Pentacarboxy III di(tris(hydroxymethyl)methanamide)
Pentacarboxy III poly(tris(hydroxymethyl)methanamide)
Pentacarboxy III mono(D-gluosamide)
Pentacarboxy III di(D-gluosamide)
Pentacarboxy III poly(D-gluosamide)
Hexacarboxy I mono(ethanolamide)
Hexacarboxy I di(ethanolamide)
Hexacarboxy I poly(ethanolamide)
Hexacarboxy I mono(bis(hydroxymethyl)methanamide)
Hexacarboxy I di(bis(hydroxymethyl)methanamide)
Hexacarboxy I poly(bis(hydroxymethyl)methanamide)
Hexacarboxy I mono(tris(hydroxymethyl)methanamide)
Hexacarboxy I di(tris(hydroxymethyl)methanamide)
Hexacarboxy I poly(tris(hydroxymethyl)methanamide)
Hexacarboxy I mono(D-gluosamide)
Hexacarboxy I di(D-gluosamide)
Hexacarboxy I poly(D-gluosamide)
Hexacarboxy III mono(ethanolamide)
Hexacarboxy III di(ethanolamide)
Hexacarboxy III poly(ethanolamide)
Hexacarboxy III mono(bis(hydroxymethyl)methanamide)
Hexacarboxy III di(bis(hydroxymethyl)methanamide)
Hexacarboxy III poly(bis(hydroxymethyl)methanamide)
Hexacarboxy III mono(tris(hydroxymethyl)methanamide)
Hexacarboxy III di(tris(hydroxymethyl)methanamide)
Hexacarboxy III poly(tris(hydroxymethyl)methanamide)
Hexacarboxy III mono(D-gluosamide)
Hexacarboxy III di(D-gluosamide)
Hexacarboxy III poly(D-gluosamide)
Heptacarboxy I mono(ethanolamide)
Heptacarboxy I di(ethanolamide)
Heptacarboxy I poly(ethanolamide)
Heptacarboxy I mono(bis(hydroxymethyl)methanamide)
Heptacarboxy I di(bis(hydroxymethyl)methanamide)
Heptacarboxy I poly(bis(hydroxymethyl)methanamide)
Heptacarboxy I mono(tris(hydroxymethyl)methanamide)
Heptacarboxy I di(tris(hydroxymethyl)methanamide)
Heptacarboxy I poly(tris(hydroxymethyl)methanamide)
Heptacarboxy I mono(D-gluosamide)
Heptacarboxy I di(D-gluosamide)
Heptacarboxy I poly(D-gluosamide)
5,10,15,20-tetracarboxyphenylporphin mono(ethanolamide)
5,10,15,20-tetracarboxyphenylporphin di(ethanolamide)
5,10,15,20-tetracarboxyphenylporphin tri(ethanolamide)
5,10,15,20-tetracarboxyphenylporphin tetra(ethanolamide)
5,10,15,20-tetracarboxyphenylporphin mono(bis(hydroxymethyl) methanamide)
5,10,15,20-tetracarboxyphenylporphin di(bis(hydroxymethyl) methanamide)
5,10,15,20-tetracarboxyphenylporphin tri(bis(hydroxymethyl) methanamide)
5,10,15,20-tetracarboxyphenylporphin tetra(bis(hydroxymethyl) methanamide)
5,10,15,20-tetracarboxyphenylporphin mono(tris(hydroxymethyl) methanamide)
5,10,15,20-tetracarboxyphenylporphin di(tris(hydroxymethyl) methanamide)
5,10,15,20-tetracarboxyphenylporphin tri(tris(hydroxymethyl) methanamide)

5,10,15,20-tetracarboxyphenylporphin tetra(tris(hydroxymethyl)methanamide)
5,10,15,20-tetracarboxyphenylporphin mono(D-glucosamide)
5,10,15,20-tetracarboxyphenylporphin di(D-glucosamide)
5,10,15,20-tetracarboxyphenylporphin tri(D-glucosamide)
5,10,15,20-tetracarboxyphenylporphin tetra(D-glucosamide)
5,10,15-tricarboxyphenyl-20-phenylporphin mono(ethanolamide)
5,10,15-tricarboxyphenyl-20-phenylporphin di(ethanolamide)
5,10,15-tricarboxyphenyl-20-phenylporphin tri(ethanolamide)
5,10,15-tricarboxyphenyl-20-phenylporphin mono(bis(hydroxymethyl)methanamide)
5,10,15-tricarboxyphenyl-20-phenylporphin di(bis(hydroxymethyl)methanamide)
5,10,15-tricarboxyphenyl-20-phenylporphin tri(bis(hydroxymethyl)methanamide)
5,10,15-tricarboxyphenyl-20-phenylporphin mono(tris(hydroxymethyl)methanamide)
5,10,15-tricarboxyphenyl-20-phenylporphin di(tris(hydroxymethyl)methanamide)
5,10,15-tricarboxyphenyl-20-phenylporphin tri(tris(hydroxymethyl)methanamide)
5,10,15-tricarboxyphenyl-20-phenylporphin mono(D-glucosamide)
5,10,15-tricarboxyphenyl-20-phenylporphin di(D-glucosamide)
5,10,15-tricarboxyphenyl-20-phenylporphin tri(D-glucosamide)
5,10-dicarboxyphenyl-15,20-diphenylporphin mono(ethanolamide)
5,10-dicarboxyphenyl-15,20-diphenylporphin di(ethanolamide)
5,10-dicarboxyphenyl-15,20-diphenylporphin mono(bis(hydroxymethyl)methanamide)
5,10-dicarboxyphenyl-15,20-diphenylporphin di(bis(hydroxymethyl)methanamide)
5,10-dicarboxyphenyl-15,20-diphenylporphin mono(tris(hydroxymethyl)methanamide)
5,10-dicarboxyphenyl-15,20-diphenylporphin mono(tris(hydroxymethyl)methanamide)
5,10-dicarboxyphenyl-15,20-diphenylporphin di(tris(hydroxymethyl)methanamide)
5,10-dicarboxyphenyl-15,20-diphenylporphin mono(D-glucosamide)
5,10-dicarboxyphenyl-15,20-diphenylporphin di(D-glucosamide)
5,15-dicarboxyphenyl-10,20-diphenylporphin mono(ethanolamide)
5,15-dicarboxyphenyl-10,20-diphenylporphin di(ethanolamide)
5,15-dicarboxyphenyl-10,20-diphenylporphin mono(bis(hydroxymethyl)methanamide)
5,15-dicarboxyphenyl-10,20-diphenylporphin di(bis(hydroxymethyl)methanamide)
5,15-dicarboxyphenyl-10,20-diphenylporphin mono(tris(hydroxymethyl)methanamide)
5,15-dicarboxyphenyl-10,20-diphenylporphin di(tris(hydroxymethyl)methanamide)
5,15-dicarboxyphenyl-10,20-diphenylporphin mono(D-glucoseamide)
5,15-dicarboxyphenyl-10,20-diphenylporphin di(D-gluosamide)
5-carboxyphenyl-10,15,20-triphenylporphin ethanolamide
5-carboxyphenyl-10,15,20-triphenylporphin bis(hydroxymethyl) methanamide
5-carboxyphenyl-10,15,20-triphenylporphin tris(hydroxymethyl) methanamide
5-carboxyphenyl-10,15,20-triphenylporphin D-glucosamide The following examples illustrate the usefulness of the compounds of the present invention for photodetection and phototherapy.

EXAMPLE 12

Selective accumulation within tumor tissue (B6D2)F1 mice bearing subcutaneous transitional cell carcinoma FCB were each injected intraperitoneally with 10 mg per kg body weight every other day for 10 days, for a total dose of 50 mg per kg body weight of a compound selected from: mesoporphyrin IX di(ethanolamide), mesoporphyrin IX di(bis(hydroxymethyl)methanamide), mesoporphyrin IX di(tris(hydroxymethyl)methanamide), hematoporphyrin IX di(methylether) di(ethanolamide), hematoporphyrin IX di(ethylether) di(ethanolamide), hematoporphyrin IX di(propylether) di(ethanolamide) and deuteroporphyrin IX di(ethanolamide).

The mice were then killed and their tissues examined for porphyrin fluorescence under UV light 48 hours following the final injection. All of the compounds tested showed strong fluorescence in the necrotic areas of the tumor with little or no fluorescence in the adjacent healthy tissues. Significant fluorescence was also observed in the pancreas, but no fluorescence was observed in the skin, bowel, skeletal muscle, lungs, heart, thymus, liver, spleen or kidneys. Tissues that contained the modified mesoporphyrins which showed porphyrin fluorescence at autopsy continued to do so for at least several weeks of storage in buffered formalin, but tissues containing the hematoporphyrin derivatives completely lost their original porphyrin fluorescence while stored in buffered formalin in the dark.

EXAMPLE 13

Selective accumulation within tumor tissue

The procedures of Example 12 were repeated on (B6D2)F1 mice bearing Lewis lung carcinoma. 100 mg of hematoporphyrin IX di(propylether) di(ethanolamide) per kg body weight was injected over a 10 days period. At autopsy, intense porphyrin fluorescence was observed in the necrotic areas of the tumors with very little fluorescence in other locations except the pancreas.

EXAMPLE 14

Potency of the photosensitizers (photohemolysis method)

Human erythrocytes washed three times in tris-buffered saline were placed in plastic dishes along with appropriate concentrations of compound selected from: mesoporphyrin IX (di(tris(hydroxymethyl)methanamide), hematoporphyrin IX di(methylether) di(ethanolamide), hematoporphyrin IX (di(ethylether) di(ethanolamide), hematoporphyrin IX di(propylether) di(ethanolamide), hematoporphyrin IX di(butylether) di(ethanolamide), hematoporphyrin IX di(isobutylether), di(ethanolamide), deuteroporphyrin IX di(ethanolamide) and, as reference compounds, hematoporphyrin IX and polyhematoporphyrin. Following 30 min. dark incubation at room temperature, the dishes were illuminated from below for 5 to 10 min. by placing them on a clear Lucite platform 2 cm above daylight fluorescent lamps. Following illumination, dishes incubated in the dark were analyzed for percent hemolysis.

Table II shows the percent of hemolysis caused by 5 min. illumination in the presence of the sensitizers at 100 μM concentration in aqueous solutions at various pH. These data show that most compounds of the present invention are better photosensitizers at physiological pH than polyhematoporphyrin which is equivalent to the active ingredient of the compound actually used for photodynamic therapy (i.e. Photofrin ® II).

TABLE II

| Sensitizers | % hemolysis | | |
|---|---|---|---|
| | pH 7.40 | pH 6.50 | pH 5.60 |
| Mesoporphyrin IX di(ethanolamide) | 19.1 | 21.5 | 6.1 |
| Mesoporphyrin IX di(bis(hydroxymethyl)methanamide) | 38.1 | 51.7 | 94.1 |
| Mesoporphyrin IX di(tris(hydroxymethyl)methanamide) | 92.8 | 65.8 | 82.7 |
| Hematoporphyrin IX di(methylether) di(ethanolamide) | 31.2 | 25.0 | 21.9 |
| Hematoporphyrin IX di(ethylether) di(ethanolamide) | 47.9 | 66.2 | 70.7 |
| Hematoporphyrin IX di(propylether) di(ethanolamide) | 46.3 | 100.0 | 71.0 |
| Hematoporphyrin IX di(butylether) di(ethanolamide) | 47.8 | 89.5 | 85.4 |
| Hematoporphyrin IX di(isobutylether) di(ethanolamide) | 16.1 | 67.1 | 70.4 |
| Deuteroporphyrin IX di(ethanolamide) | 99.6 | 100.0 | 89.7 |
| Hematoporphyrin IX | 17.5 | 94.6 | 100.0 |
| Polyhematoporphyrin | 12.0 | 22.3 | 38.5 |

EXAMPLE 15

Dark toxicity of compounds

Eight (B6D2)F1 mice were maintained in the dark and were intraperitoneally injected with hematoporphyrin IX di(propylether) di(ethanolamide) at a dose rate of 10 mg per kg body weight on each of three successive days. There was no apparent toxicity.

The experiment was repeated on a second set of mice into which 10 mg/kg body weight hematoporphyrin IX (di(propylether) di(ethanolamide) was injected daily for six successive days. There was no apparent toxicity.

The experiment was repeated on a third set of mice into which 100 mg/kg body weight hematoporphyrin IX di(propylether) di(ethanolamide) was injected daily for three days. There was definite toxicity, but no death.

EXAMPLE 16

Therapeutic effects in the dark

Hematoporphyrin IX di(propylether) di(ethanolamide) at a concentration of 1.0 mg per mL in 10% DMSO in serum was injected intravenously into Skh:HR-1 mice bearing well-developed Adenocarcinoma 755 (a) in ascites form, or (b) as a solid tumor growing within the muscles of the thigh, and also into Skh:HR-1 mice bearing advanced subcutaneous tumors of FCB transitional cell carcinoma of the bladder. The dose in each case was 10 mg per kg of body weight. The mice were maintained in dim light following the injection, to minimize the possibility of photodynamic effects. In each case a small proportion of the injected mice showed a rapid and complete regression of the cancer, such regression being maintained until termination of the experiment 10 weeks later. Cancers in control mice normally grew progressively. However, please note that the particular tumor/mouse combination used is not completely histocompatible and therefore may provide an unusually sensitive detection system for anti-tumor activity in the dark.

EXAMPLE 17

Phototherapeutic effectiveness

Lewis Lung Carcinoma was transplanted subcutaneously into the flank of Skh:HR-1 hairless mice, and allowed to grow until the tumor was approximately 10 mm in diameter. A dose of 10 mg per kg of body weight of Hematoporphyrin IX di(propylether) di(ethanolamide) was then injected intraperitoneally. One day later, the tumor and adjacent normal skin was exposed to a dose of 50 mWhr/cm² photoactivating light (wavelengths greater than 600 nm) at an intensity of 200 mW/cm².

Immediately following exposure of the photoactivating light, the tumor was noted to have changed colour, and there was obvious edema within the tumor. Within the next 24 hours, the skin covering the centre of the tumor became necrotic but the skin immediately adjacent showed only mild phototoxic damage. Since both areas of skin received similar doses of photoactivating light, hematoporphyrin IX di(propylether) di(ethanolamide) appears to have a clinically useful degree of tissue specificity. Six days after exposure to the photoactivating light, there was no evidence of residual tumor.

Hence, it is shown by the procedures described in Examples 12 to 17 that the compounds of the present invention are valuable for photodetection and phototherapy of tumor, cancer and malignant tissue. These compounds can be administered by the oral, intravenous or intramuscular routes. They can also be topically applied. The solvent or delaying media are those used for other pharmaceutical compounds and are well known to those skilled in the art.

We claim:

1. A therapeutic composition for the detection and treatment of tumors and malignant tissue sensitive thereto, comprising a therapeutically effective quantity of mono-, di- or polyamides of an amino alcohol and a cyclic tetrapyrrole, the general structure of which is:

$$(ZNHCO)_n X$$

wherein:
Z is the amino alcohol molecule less the amino group and is selected from mono-, di-, and polyhydroxyalkyl residues with the provisio that Z does not include a carboxyl group;

X is selected from substituted tetrapyrroles in which the substituent is at least one of the group consisting of methyl, ethyl, vinyl, hydroxyethyl, alkoxyethyl, methylcarboxy, ethylcarboxy, Z-substituted propylamide, phenyl and $(ZNHCO)_n$-substituted phenylamide, and n is an integer from 1 to 8.

2. A therapeutic composition as claimed in claim 1 wherein the tetrapyrrole compound is of the formula:

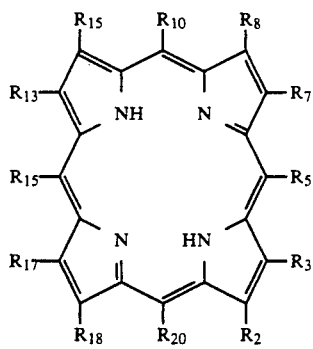

or the corresponding di- or tetrahydropyrroles and wherein $R_2$ is H, $CO_2H$ or $CH_2CH_2CO_2H$
$R_3$ is H, $CH_3$ or $CH_2CO_2H$
$R_5$ is H, $C_6H_5$, $C_6H_4CH_3$ or $C_6H_4CO_2H$
$R_7$ is H, $CH_2CH_3$, $CH=CH_2$, $CH_2CH_2CO_2H$, $CH(OH)CH_3$ or $CH(OR)CH_3$
$R_8$ is H, $CH_3$, $CH_2CO_2H$
$R_{10}$ is H, $C_6H_5$, $C_6H_4CH_3$ or $C_6H_4CO_2H$
$R_{12}$ is H, $CH_2CH_3$, $CH=CH_2$, $CH_2CH_2CO_2H$, $CH(OH)CH_3$ or $CH(OR)CH_3$
$R_{13}$ is H, $CH_3$ or $CH_2CO_2H$
$R_{15}$ is H, $CH_6H_5$, $C_6H_4CH_3$ or $C_6H_4CO_2H$
$R_{17}$ is H, $CH_3$, $CH_2CO_2H$ or $CH_2CH_2CO_2H$
$R_{18}$ is H, $CH_3$, $CH_2CO_2H$ or $CH_2CH_2CO_2H$
$R_{20}$ is H, $CH_2CO_2H$, $C_6H_5$, $C_6H_4CH_3$ or $C_6H_4CO_2H$
and a pharmaceutically acceptable carrier therefor.

3. A composition as claimed in claim 2 wherein said amino alcohol is selected from 2-aminoethanol, 2-amino-1,3-propanediol, 2-amino-2-(hydroxymethyl)-1,3-propanediol and D-glucosamine.

4. A composition as claimed in claim 2 wherein said tetrapyrrole is selected from coproporphyrin I and III, deuteroporphyrin IX, hematoporphyrin IX, hematoporphyrin IX di(alkylether), mesoporphyrin IX, protoporphyrin IX, uroporphyrin IX, chlorin e6, pentacarboxyporphyrin I and III, hexacarboxyporphyrin I and III, heptacarboxyporphyrin I, meso-tetracarboxyphenylporphin, meso-tricarboxyphenyl-phenylporphin, meso-dicarboxyphenyl-diphenylporphin, meso-carboxyphenyl-triphenylporphin.

5. A composition as claimed in claim 3 wherein said tetrapyrrole is selected from coproporphyrin I, coproporphyrin III, deuteroporphyrin IX, hematoporphyrin IX, hematoporphyrin IX di(alkylether), hematoporphyrin IX di(methylether), hematoporphyrin IX di(ethylether), hematoporphyrin IX di(propylether), hematoporphyrin IX di(butylether), hematoporphyrin IX di(isobutylether), mesoporphyrin IX, protoporphyrin IX, uroporphyrin IX, chlorin e6, pentacarboxyporphyrin I, pentacarboxyporphyrin III, hexacarboxyporphyrin I, hexacarboxyporphyrin III, heptacarboxyporphyrin I, meso-tetracarboxyphenylporphin, meso-tricarboxyphenyl-phenylporphin, meso-dicarboxyphenyl-diphenylporphin, and meso-carboxyphenyltriphenylporphin.

6. A composition as claimed in claim 2 wherein said amide is selected from mesoporphyrin IX di(ethanolamide), mesoporphyrin IX di(bis(hydroxymethyl)methanamide), mesoporphyrin IX di(tris(hydroxymethyl)methanamide), deuteroporphyrin IX di(ethanolamide), deuteroporphyrin IX di(bis(hydroxymethyl)methanamide), deuteroporphyrin IX di(tris(hydroxymethyl)methanamide), hematoporphyrin IX di(ethanolamide), hematoporphyrin IX di(bis(hydroxymethyl)methanamide), hematoporphyrin IX di(tris(hydroxymethyl)methanamide), hematoporphyrin di(alkylether) di(ethanolamide), hematoporphyrin IX di(alkylether) di(bis(hydroxymethyl)methanamide), hematoporphyrin IX di(alkylether) di(tris(hydroxymethyl)methanamide), hematoporphyrin IX di(methylether) di(ethanolamide), hematoporphyrin IX di(methylether) di(bis(hydroxymethyl)methanamide), hematoporphyrin IX di(methylether) di(tris(hydroxymethyl)methanamide), hematoporphyrin IX di(ethylether) di(ethanolamide), hematoporphyrin IX di(ethylether) di(bis(hydroxymethyl)methanamide), hematoporphyrin IX di(ethylether) di(tris(hydroxymethyl)methanamide, hematoporphyrin IX (dipropylether) di(ethanolamide), hematoporphyrin IX (dipropylether) di(bis(hydroxymethyl)methanamide, hematoporphyrin IX (dipropylether) di(tris(hydroxymethyl)methanamide), hematoporphyrin IX (dibutylether) di(ethanolamide), hematoporphyrin IX (dibutylether) di(bis(hydroxymethyl)methanamide), hematoporphyrin IX (dibutylether) di(tris(hydroxymethyl)methanamide, hematoporphyrin IX (diisobutylether) di(ethanolamide), hematoporphyrin IX (diisobutylether) di(bis(hydroxymethyl)methanamide and hematoporphyrin IX (diisobutylether) di(tris(hydroxymethyl)methanamide.

7. A method for detecting malignant tissue abnormalities in a patient comprising administering to said patient an effective amount of a tetrapyrrole derivative of an amino alcohol as claimed in claim 1, exposing said tissue abnormality to at least one of Ultra violet and visible light and detecting the presence of said abnormality by fluorescence.

8. A method as claimed in claim 7 wherein said tetrapyrrole derivative is selected from a composition as claimed in claim 2.

9. A method for treating malignant tissue abnormalities in a patient comprising administering to said patient an effective amount of a tetrapyrrole derivative of an amino alcohol as claimed in claim 1, and exposing said tissue abnormalty to light within the photoactivating spectrum of said tetrapyrrole derivative.

10. A method as claimed in claim 9 wherein said tetrapyrrole derivative is selected from a composition as claimed in claim 2.

* * * * *

UNITED STATES PATENT AND TRADEMARK OFFICE
CERTIFICATE OF CORRECTION

PATENT NO. : 5,219,878
DATED : June 15, 1993
INVENTOR(S) : Ringuet et al.

It is certified that error appears in the above-identified patent and that said Letters Patent is hereby corrected as shown below:

In claim 2, column 19, line 1 of the Patent, in the upper left corner of the tetrapyrrole compound, change "$R_{15}$" to --$R_{12}$--.

Signed and Sealed this

Fifteenth Day of October, 1996

Attest:

BRUCE LEHMAN

Attesting Officer

Commissioner of Patents and Trademarks